(12) United States Patent
Lykke et al.

(10) Patent No.: US 9,233,019 B2
(45) Date of Patent: Jan. 12, 2016

(54) OSTOMY APPLIANCE WITH MULTIPLE RELEASE LINERS

(75) Inventors: Mads Lykke, Broenshoej (DK); Esben Stroebech, Hoersholm (DK); Anders Bach, Copenhagen S (DK); Astrid Toftkaer, Soeborg (DK); Hasse Buus, Humlebaek (DK); Tom Kongebo, Humlebaek (DK)

(73) Assignee: Coloplast A/S, Humlebaek (DK)

( * ) Notice: Subject to any disclaimer, the term of this patent is extended or adjusted under 35 U.S.C. 154(b) by 820 days.

(21) Appl. No.: 12/452,360

(22) PCT Filed: Jun. 17, 2008

(86) PCT No.: PCT/DK2008/050145
§ 371 (c)(1),
(2), (4) Date: Apr. 23, 2010

(87) PCT Pub. No.: WO2009/000273
PCT Pub. Date: Dec. 31, 2008

(65) Prior Publication Data
US 2010/0217215 A1    Aug. 26, 2010

(30) Foreign Application Priority Data

Jun. 25, 2007  (DK) ................................ 2007 00911
Jul. 6, 2007  (DK) ................................ 2007 01003

(51) Int. Cl.
*A61F 5/44*  (2006.01)
*A61F 5/443*  (2006.01)
(Continued)

(52) U.S. Cl.
CPC .............. *A61F 5/4404* (2013.01); *A61F 5/443* (2013.01); *A61F 5/445* (2013.01); *A61L 15/225* (2013.01);
(Continued)

(58) Field of Classification Search
USPC .................................................. 604/344, 336
See application file for complete search history.

(56) References Cited

U.S. PATENT DOCUMENTS 3,081,771 A * 3/1963 Lee ................................ 604/344
4,123,409 A * 10/1978 Kaelble ........................ 523/118
(Continued)

FOREIGN PATENT DOCUMENTS

CN  101588775 A  11/2009
EP  0 051 935  5/1982
(Continued)

OTHER PUBLICATIONS

WO2007128320_ISR_Written_Opinion_ISA.pdf.; IPRP for PCT/DK2007/050055, published by WIPO issuance date Nov. 11, 2008.*
(Continued)

*Primary Examiner* — Tatyana Zalukaeva
*Assistant Examiner* — Guy Townsend
(74) *Attorney, Agent, or Firm* — Coloplast Corp., Coloplast A/S; Nick Baumann (57) ABSTRACT

An ostomy appliance for attachment to the stoma body comprising a soft adhesive wafer (1) having a tensile strength at 20% strain of less than 0.75N/4 mm and a collecting pouch attachable to an adhesive wafer, the wafer comprises a backing layer and a skin-facing adhesive layer, wherein the adhesive skin-facing surface of the wafer is provided with at least two release liners (3, 4) each covering at least a part of the adhesive surface and together covering the entire adhesive surface.

14 Claims, 3 Drawing Sheets

(51) Int. Cl.
*A61F 5/445* (2006.01)
*A61L 15/22* (2006.01)
*A61L 15/26* (2006.01)
*A61L 15/42* (2006.01)
*A61L 24/00* (2006.01)
*A61L 24/04* (2006.01)

(52) U.S. Cl.
CPC .............. *A61L 15/26* (2013.01); *A61L 15/425* (2013.01); *A61L 24/0036* (2013.01); *A61L 24/043* (2013.01); *A61L 24/046* (2013.01)

(56) References Cited

U.S. PATENT DOCUMENTS

| | | | |
|---|---|---|---|
| 4,419,100 A | | 12/1983 | Alexander |
| 4,445,898 A | * | 5/1984 | Jensen .......................... 604/337 |
| 4,657,986 A | * | 4/1987 | Isayama et al. ............... 525/407 |
| 4,701,169 A | * | 10/1987 | Steer ............................. 604/344 |
| 4,826,495 A | * | 5/1989 | Petersen ....................... 604/333 |
| 4,894,058 A | * | 1/1990 | Jensen .......................... 604/332 |
| 5,051,259 A | * | 9/1991 | Olsen et al. .................. 424/443 |
| 5,074,852 A | | 12/1991 | Castellana et al. |
| 5,384,174 A | * | 1/1995 | Ward et al. ................... 428/41.5 |
| 5,473,026 A | * | 12/1995 | Strong et al. ................. 525/477 |
| 5,722,965 A | * | 3/1998 | Kuczynski .................... 604/344 |
| 6,140,548 A | | 10/2000 | Hansen et al. |
| 6,248,915 B1 | * | 6/2001 | Ito et al. ........................ 556/445 |
| 6,332,879 B1 | * | 12/2001 | Nielsen et al. ................ 604/344 |
| 6,420,008 B1 | * | 7/2002 | Lewis et al. ................... 428/78 |
| 6,548,727 B1 | | 4/2003 | Swenson |
| 6,709,421 B1 | * | 3/2004 | Falconer ....................... 604/335 |
| 6,846,508 B1 | * | 1/2005 | Colas et al. ................... 427/2.31 |
| 6,977,323 B1 | | 12/2005 | Swenson |
| 7,070,580 B2 | * | 7/2006 | Nielsen ......................... 604/180 |
| 7,160,275 B2 | * | 1/2007 | Falconer ....................... 604/333 |
| 7,422,578 B2 | * | 9/2008 | Shan et al. .................... 604/342 |
| 7,842,752 B2 | * | 11/2010 | Bougherara ................... 524/588 |
| 7,862,878 B2 | * | 1/2011 | Stroebech et al. ............ 428/137 |
| 7,919,182 B2 | * | 4/2011 | Hamada et al. ............. 428/355 R |
| 8,076,528 B2 | * | 12/2011 | Lam et al. ..................... 602/56 |
| 8,277,427 B2 | * | 10/2012 | Edvardsen et al. ........... 604/355 |
| 2004/0127832 A1 | | 7/2004 | Sigurjonsson et al. |
| 2007/0020319 A1 | * | 1/2007 | Bougherara .................. 424/445 |
| 2008/0171958 A1 | | 7/2008 | Gundersen |
| 2008/0311396 A1 | * | 12/2008 | Hamada et al. ........... 428/355 EN |
| 2009/0306571 A1 | * | 12/2009 | Lam et al. ..................... 602/56 |
| 2010/0168693 A1 | * | 7/2010 | Edvardsen et al. ........... 604/355 |
| 2010/0217215 A1 | * | 8/2010 | Lykke et al. .................. 604/344 |
| 2011/0245789 A1 | | 10/2011 | Buus |
| 2013/0090617 A1 | * | 4/2013 | Uveborn ....................... 604/344 |
| 2013/0261576 A1 | * | 10/2013 | Strobech et al. ............. 604/342 |

FOREIGN PATENT DOCUMENTS

| | | | | |
|---|---|---|---|---|
| EP | 0 228 191 | A2 | 7/1987 | |
| EP | 0 231 508 | | 8/1987 | |
| EP | 0 259 184 | A1 * | 3/1988 | .............. A61F 5/441 |
| EP | 0259184 | * | 3/1988 | .............. A61F 5/441 |
| EP | 0 434 258 | | 6/1991 | |
| EP | 0 465 023 | A1 | 1/1992 | |
| EP | 0 674 890 | A2 | 10/1995 | |
| EP | 0259184 | A1 * | 9/1998 | |
| EP | 1679085 | A2 | 7/2006 | |
| EP | 2 018 161 | | 1/2009 | |
| GB | 2 128 479 | | 5/1984 | |
| GB | 2226761 | | 7/1990 | |
| JP | 2004 067720 | A | 3/2004 | |
| WO | WO 89/11262 | | 11/1989 | |
| WO | WO 93/08777 | | 5/1993 | |
| WO | WO 98/55157 | A2 * | 12/1998 | .............. A61L 15/00 |
| WO | WO9855157 | * | 12/1998 | .............. A61L 15/00 |
| WO | WO9855157 | A2 * | 12/1998 | |
| WO | WO 99/16396 | | 4/1999 | |
| WO | WO 00/44324 | | 8/2000 | |
| WO | WO 00/61040 | * | 10/2000 | .............. A61F 5/451 |
| WO | WO0061040 | * | 10/2000 | .............. A61L 5/443 |
| WO | WO0061040 | A1 * | 10/2000 | |
| WO | WO 02/066087 | A1 | 8/2002 | |
| WO | 2004029174 | A1 | 4/2004 | |
| WO | WO2005021058 | * | 3/2005 | .............. A61L 15/58 |
| WO | WO2005021058 | A2 * | 3/2005 | |
| WO | WO2005021058 | A2 * | 3/2005 | .............. A61L 15/58 |
| WO | WO 2005/032401 | A2 | 4/2005 | |
| WO | WO2005032401 | * | 4/2005 | .............. A61L 15/00 |
| WO | WO2005032401 | A2 * | 4/2005 | ................ A61F 5/44 |
| WO | WO2005032401 | A2 * | 4/2005 | |
| WO | 2005054306 | A1 | 6/2005 | |
| WO | 2006089551 | A1 | 8/2006 | |
| WO | WO2006089551 | * | 8/2006 | |
| WO | WO2006089551 | A1 * | 8/2006 | |
| WO | WO 2007/128320 | | 11/2007 | |
| WO | WO 2007/128320 | A2 | 11/2007 | |

OTHER PUBLICATIONS

R.Byron Bird et al, "Dynamics of Polymeric Liquids", vol. 1, Fluid Mechanics, $2^{nd}$ Ed., 1987, pp. 112-117.
Dansk Standard, "Plastics—Determination of tensile properties" DS/EN ISO 527-1, Jun. 15, 1993.
Coloplast Advertisement, "Coloplast Because the Body Heals Faster than the Mind", Ostomy Quarterly, Fall 1986, 2 pages.
International Standard, Plastics of Tensile Properties, ISO 527-1, First Edition, Jun. 15, 1993, ISO Reference No. ISO 527-1;1993(E), 15 pages.

* cited by examiner

OSTOMY APPLIANCE WITH MULTIPLE RELEASE LINERS

This is a national stage of PCT/DK08/050,145 filed Jun. 17, 2008 and published in English, which has a priority of Denmark no. PA 2007 00911 filed Jun. 25, 2007 and Denmark no. PA 2007 01003 filed Jul. 6, 2007, hereby incorporated by reference.

BACKGROUND OF THE INVENTION

1. Field of the Invention

The invention relates to an ostomy appliance for attachment to the body and for collecting bodily waste discharged from a stoma.

Ostomy appliances are usually in the form of a receptacle, e.g. a bag, pouch or for receiving the waste, connected to an adhesive wafer that can be attached to the skin of the patient. The wafer is typically in the form of a backing layer coated on the skin-facing surface with an adhesive layer and the wafer is further provided with an aperture for accommodating the stoma. The size and shape of said aperture can often be adapted individually to fit the anatomy of the patient.

One of the crucial parts of such appliances is the adhesive wafer. The wafer should be able to fit leak proof around the body opening and have good adherence to the skin without unintended detachment from the skin, but at the same time the wafer should be easy to remove again without damaging the skin. Furthermore, the wafer should be able to follow the movements of the body and be comfortable to wear. The components of the wafer, the adhesive and the backing layer determine these properties.

The adhesive of such appliances is usually a hydrocolloid adhesive coated in a relatively thick layer on a backing layer and combined with the fact that this adhesive has a high modulus, the appliance may be inflexible and bulky to wear.

The wafer of an ostomy appliance may be made softer by exchanging the hydrocolloid adhesive with a softer adhesive, e.g. a soft adhesive. However, providing an ostomy appliance with a soft adhesive may give rise to new problems. Whereas the conventional hydrocolloid adhesive wafer was rather stiff and thereby easy to handle and apply, the soft adhesive wafers are soft and mechanical unstable and may easily fold and stick to itself during application.

When applying an adhesive wafer around a stoma the conventional hydrocolloid adhesive wafers are relatively stable and easy to handle, even when the release liner is removed prior to application. The construction of the current hydrocolloid adhesives in modern stoma care products are carried out in such a manner that the wafer, when the release liner is removed, is stiff enough in order for the product to stay in an almost planar manner. In other words the product does not bend, curl or fold significantly during application.

This is due to the choice of backing layer and adhesive. The backing layer is usually a relatively stiff polymer backing and the adhesive is a polymer based continuous phase filled with particles that add to the modulus of the adhesive. The combination of a high modulus backing and adhesive makes the adhesive wafer very stiff.

Due to the choice of backing layer, a relatively stiff polymer backing layer stabilizes the product in combination with a hydrocolloid adhesive. The presence of an absorbent filler, such as hydrocolloid particles, makes the adhesive stiffer. A polymeric matrix for the adhesive comprising PIB (polyisobutylene), SIS (styrene isoprene styrene block copolymer), resin etc. produces a relatively stiff adhesive.

When the type of adhesive is changed from the highly filled relatively stiff materials to a soft, low or non filled adhesive, the need for a soft backing layer is essential in order to obtain the right properties for the intended use. This makes the adhesive wafer very soft, flexible and unable to hold itself in a relatively planar manner after removal of the release liner. The adhesive wafer itself is so flexible that the side portions of the wafer will bend down with gravity after removal of release liner, resulting in the adhesive to stick to itself, bend, curl or fold and the wafer will be useless.

2. Description of the Related Art

Handling soft and/or thin adhesive wafers or dressings may be addressed in different ways. The adhesive surface may be covered with a number of release liners or the backing layer may be provided with detachable support means.

Wound care dressings are often provided with two release liners, each covering an area of the product. Hereby, the user can remove one release liner, attach the exposed adhesive surface to the body and then remove the second liner and apply the rest of the dressing, all the way through without touching the dressing with the fingers. This solution is for hygiene purpose and is often referred to a non-touch solution.

Devices for faecal management often comprise two or more release liners in order to ease the application to the curved and complicated perianal area. This has been made to facilitate the fact that the adhesive wafer has to be bent approximately 180 degrees in order to adhere to the buttocks.

Ultra thin wound dressings may be provided with a support layer on the non-adhesive surface of the wafer. Such support layer may be in the form of a rigid or semi-rigid frame that controls the conformation of the dressing during application. When the dressing is applied, the frame is removed.

Today, conventional ostomy appliances are provided with a single release liner, covering the entire adhesive surface. A non-touch solution is achieved by having a non-adhesive tab or ear on the edge portion of the flange for holding during application without touching the adhesive. The tab or ear may be used to ease detachment of the wafer later. This solution is suited for mechanical stable wafers while soft wafers comprising soft adhesive would be difficult—not to say impossible—to handle with such release liner system.

Thus, there is still a need for an ostomy appliance having a high flexibility and comfort for the user and being easy to apply.

SUMMARY OF THE INVENTION

The present invention aims at providing a collecting ostomy appliance, which improves the patient's comfort due to the softness of the ostomy appliance and which is easy to apply.

One object of the present invention is to provide an ostomy appliance with a release liner system that facilitates easy and stepwise application of the adhesive wafer.

BRIEF DESCRIPTION OF THE DRAWINGS

The invention is disclosed more in detail with reference to the drawings.

DETAILED DESCRIPTION OF THE PRESENT INVENTION

The invention relates to an ostomy appliance for attachment to the stoma body comprising a soft adhesive wafer having a tensile strength at 20% strain of less than 0.75N/4 mm and a collecting pouch attachable to an adhesive wafer, the wafer comprises a backing layer and a skin-facing adhesive layer, wherein the adhesive skin-facing surface of the wafer is provided with at least two release liners each covering at least a part of the adhesive surface and together these liners cover the entire adhesive surface.

The soft and flexible collecting device according to the invention requires a solution for proper handling during application of the device to the skin, because the handling of a soft and flexible adhesive wafers during application is very difficult as it will bend and cannot stay in a planar position without support. By dividing the protective film or release liner into two or more separately removable liners, the first release liner may be removed and the exposed adhesive surface is applied to the body, thereby bonding the adhesive wafer partially to the skin. Then the second and optionally the third release liner are removed in order to apply the remaining adhesive surface of the wafer to the skin.

The release liner system of the appliance according to the invention renders it possible for the user to apply a very soft and flexible adhesive wafer to the skin in an easy way.

The multiple release liners that can be removed in different times during the application of the wafer facilitate easy and safe application to the peristomal skin without the risk of touching the adhesive surface.

In one embodiment of the invention three release liners cover the adhesive surface. The release liners may be in the form of two side liners covering the side portions of the wafer and a central liner covering the middle part of the wafer. When applied, the central liner is removed first, the appliance is fastened around the stoma and the two side liners are subsequently removed by sliding away from the stoma and fixing the adhesive to the skin. In this way the wafer can be applied under full control, without wrinkling or folding and without touching the adhesive with the fingers.

One of the release liners may cover the central portion of the adhesive surface. The central liner may be arranged concentric to the central aperture and the rest of the adhesive surface may be covered by two or more side liners.

The release liner system may be symmetric over the adhesive surface or it may be asymmetric.

The ostomy appliance according to the present invention is preferably provided with a layer of a soft absorbent adhesive. Examples of such adhesives may be a polyalkyleneoxide polymer and an organosiloxane based cross-linked adhesive system.

In a preferred embodiment of the invention, the adhesive comprises ethylene vinyl acetate. The adhesive comprising ethylene vinyl acetate may suitably be an adhesive known in the art such as the adhesive composition disclosed, for example in Danish Patent Application PA 2007 01003.

Handling of a very soft adhesive wafer for an ostomy appliance is eased by the present invention that allows the user to remove the release liner gradually while applying the ostomy appliance.

The ostomy appliance of the present invention comprises an adhesive wafer comprising a thin elastic, low modulus backing layer covered with a soft absorbing adhesive on one surface. The adhesive layer may be in the form of one or more layers.

Preparing the adhesive wafer with optimal adhesion properties will at the same time give rise to handling problems due to the low mechanical stability. Using a split release liner system according to the present invention solves the low mechanical stability upon application.

A two split release liner system may typically be in the form of two pre-bend side release liners each covering half of the adhesive surface of the wafer, touching each other in the midline, thus protecting the adhesive and facilitating removal of the liners partly during application of the wafer ensuring a safe, fast and easy application.

Another advantage of the split release liner system is the non-touch handling of the appliance. The non-touch handling makes it possible to apply the wafer without touching the adhesive surface.

In one embodiment of the invention, the wafer is provided with a three-split release liner system, where the two side liners are not covering the middle section of the wafer. The third middle liner covers the middle. The middle release liner may be broad, only leaving space for small side liners, which will work as non-touch tabs during application, but preferably the side liners are larger as this stabilizes the wafer and facilitates easy application. The middle release liner may preferably be substantially the same width as the attachment zone for the pouch or it may be narrower.

The use of a soft adhesive wafer in an ostomy appliance of the present invention provides completely new features to the user. Contrary to the traditional adhesive wafers comprising hydrocolloid adhesive, which is relatively high modulus, the ostomy appliance according to the invention may provide the user with greater comfort as well as lower risk of leakage. An ostomy appliance comprising such soft adhesive wafer provides an excellent attachment to the body.

By soft adhesive wafer, we mean an adhesive wafer with a tensile strength at 20% strain of less than 0.75N/4 mm using the method disclosed herein.

In a preferred embodiment of the invention, the wafer has a tensile strength at 20% strain of less than 0.5N/4 mm using the method disclosed herein.

The ostomy appliance according to the invention provides softness, flexibility, safety and comfort in wear and a good moisture transmission.

Traditional ostomy appliances comprise an adhesive wafer being rather stiff. The stiffness derives from the properties of the adhesive, as well as those of the backing film. As the skin of the stomach is exposed to large movements in the form of stretching, flexing and folding during the movements of the user it is important that the wafer is able to follow the movements of the skin.

By virtue of the fact that the adhesive layer of the ostomy appliance of the present invention is very soft, it can adhere to irregularities in the skin in a way that fluid cannot leak underneath the adhesive wafer. The ostomy appliance according to the invention is also very shapeable, which means that the edge of the opening in the component can be applied very close to a stoma without risk of irritation, strangulation or bleeding of the mucous membrane at the base of the stoma.

The adhesive wafer of the ostomy appliance according to the invention can be stretched together with the skin in a way that there is considerably less risk of shearing between skin and adhesive, which shearing can give rise to mechanical damage to the skin and unintended detachment of the ostomy appliance.

A further advantage of the ostomy appliance according to the invention is that it is adherent to skin and can be reapplied after removal from skin, because it does not to any major extent tear off skin cells during removal, which would otherwise reduce the adherent surface of the component available for reapplication. The traditionally used hydrocolloid adhesives, when removed, tear off so many skin cells that it is the surface area of the adhesive available for re-adhesions considerably decreased after removal, rendering repositioning of the appliance difficult Yet another advantage of the ostomy appliance according to the described embodiment is that it maintains its integrity upon contact with fluid. In this context it should be noted that if the opening of the ostomy appliance is too small, it could be made larger by punching or cutting in order to adapt its size to the stoma. Conventional fastening arrangements for stoma bags are often provided with cutting marks, for example in the form of helical lines, to make this kind of adaptation easier. Such adaptation of size is important for ensuring that the smallest possible area of skin around the stoma comes into contact with the intestinal content collected in the stoma bag. As already mentioned, the shapeability of the ostomy appliance means it is easy to finely adjust the shape of the opening, in a way that this coincides with the cross-sectional shape of the stoma, which may deviate from a circular shape.

The backing layer of the ostomy appliance of the present invention is preferably in the form of a polymer film, coating, laminate, textile or non-woven. The backing layer is preferably a highly flexible film being strong enough for attachment of e.g. couplings and/or pouch and for removing the ostomy appliance in one piece, but soft enough to follow the movements of the body.

The backing layer of the ostomy appliance according to the invention has preferably a force below 0.75 N/4 mm at 20% extension, preferably less than 0.5 N/4 mm, as measured using the technique described herein.

By low-modulus backing layer is meant a backing layer that has a force below 0.75 N/4 mm at 20% extension, preferably less than 0.5 N/4 mm, as measured using the technique described herein.

A preferred backing layer is a polyurethane film.

Preferably, the backing layer has thermoplastic elements that enable welding of e.g. a pouch or coupling ring to the adhesive wafer. Preferred thickness of the backing layer is between 15-60 μm in order to maintain the softness of the adhesive wafer.

The ostomy appliance of the present invention is soft and comfortable to wear, having a good adhesive tack, but is yet easy and gentle to remove and is permeable to moisture, thus overcoming the drawbacks of the hydrocolloid adhesive devices. The soft adhesive is resistant to erosion and does not loose its tack when exposed to moisture.

The ostomy appliance of the present invention is soft, comfortable and pliable due to the unique combination of a soft adhesive and a soft backing layer. The soft construction facilitates easy adaptation to scars, irregularities and skin-folds and low modulus of skin wafer. The ostomy appliance may be removed with minimal pain due to extreme flexibility and no skin cells are stripped off and thus no traumatisation of skin. The soft adhesive has a broad peel front and good tenancy during use. Reposition of adhesive is also possible without loss of tack. The adhesive is resistant to erosion and has a good water capacity due to the high water permeability and optionally use of mineral absorbers.

The adhesive of the appliance according to the present invention has a $G^*$ at 0.01 Hz less than 15.000 Pa, preferably less than 7.500 Pa as measured using the technique enclosed herein. This means that the adhesive is considerably softer than conventional adhesive systems used for attaching collecting devices to skin. Such an adhesive is soft and the produced wafer will tend to collapse under its own weight.

Another important property of the device of the invention is that the adherence force of the soft adhesive used does not change with time or changes only to a small extent with time, during wear time of the device.

It is preferred that the entire skin-facing surface of the backing layer is coated with the soft adhesive. Hereby, a soft wafer is achieved. In one embodiment of the invention, the soft adhesive may only cover the peripheral part or the central part oft the wafer. Such a wafer may have 10-90% of total area covered by the soft adhesive system and the rest covered by conventional ostomy type adhesives.

The release liners of the appliance of the present invention is preferably in the form of a polymer film, foil or paper, having release properties that enable the adhesive to be released easily from the liner. Such properties may be inherent in the material or the layer may be siliconised or coated with a low surface tension coating. Release liners are in general made on a mechanically stiff backing such as paper, polyethylene, polypropylene or polyethylene terephthalate, this stiffness will support the adhesive wafer when applying the collecting device.

As used herein a cross-link means a small region in a macromolecule (polymer chain structure) from which more than 2 chains emanate.

In a preferred embodiment of the invention the adhesive layer of the ostomy appliance of the invention may comprise a polyalkyleneoxide polymer and an organosiloxane based cross-linked adhesive system.

According to one embodiment of the invention the adhesive layer of the ostomy appliance may comprise the reaction product of:
(i) a polyalkyleneoxide polymer having one or more unsaturated end groups and
(ii) an organosiloxane comprising one or more Si—H groups, carried out in the presence of an addition reaction catalyst.

According to another embodiment of the invention the adhesive composition of the ostomy appliance comprises more than 90% w/w of the polyalkylene oxide polymer that consists of polymerised alkyleneoxide moities having three or more carbon atoms.

According to another embodiment of the invention, the adhesive composition of the ostomy appliance comprises the reaction product of:
(i) a polyalkyleneoxide polymer having at least two unsaturated end groups and wherein more than 90% w/w of the polyalkylene oxide polymer consists of polymerised alkyleneoxide moities having three or more carbon atoms,
(ii) a polysiloxane cross-linking agent comprising 3 or more Si—H groups and optionally
(iii) a polysiloxane chain extender comprising up to 2 Si—H groups carried out in the presence of an addition reaction catalyst.

According to a preferred embodiment of the invention, the addition reaction catalyst is a Pt vinyl siloxane complex.

According to a preferred embodiment of the invention, the polyalkylene oxide polymer is polypropyleneoxide.

According to a further preferred embodiment of the invention, the weight percent of polyalkylene oxide in said reaction product is 60% or above.

The polyalkylene oxide polymer having one or more unsaturated groups may be branched or linear.

However, suitably, the polyalkylene oxide polymer is linear and has two unsaturated end groups.

In one particular embodiment of the invention the polyalkylene oxide polymer is polypropyleneoxide.

The polypropylene oxide having unsaturated end groups may be a compound of formula $$CH_2=C(R^1)-(Z)-O-(X)_n-(W)-C(R^2)=CH_2 \quad (Ia)$$

or $$CH(R^1)=CH-(Z)-O-(X)_n-(W)-CH=CH(R^2) \quad (Ib)$$

wherein $R^1$ and $R^2$ are independently selected from hydrogen and $C_{1-6}$-alkyl;
Z and W is $C_{1-4}$-alkylene;
X is $-(CH_2)_3-O-$ or $-CH_2-CH(CH_3)-O-$; and
n is 1-900, more preferred 10-600, or most preferred 20-600.

The number average molecular weight of the polyalkylene oxide having unsaturated end groups is suitably between 500 and 100.000, more preferred between 500 and 50.000 and most preferred between 1.000 and 35.000.

Polypropylene oxide having unsaturated end groups may be prepared as described in U.S. Pat. No. 6,248,915 and WO No. 05/032401 or analogously to the methods described therein. Other polyalkylene oxide polymers may be prepared analogously.

The polysiloxane cross-linking agent comprising 3 or more Si—H groups is suitable a compound having the formula $$R-SiO(R,R)-(SiO(R,R))_m-Si-(R,R,R) \quad (II)$$

wherein at least three of the groups R are hydrogen and the rest of the groups R are each independently selected from $C_{1-12}$-alkyl, $C_{3-8}$-cycloalkyl, $C_{6-14}$-aryl, and $C_{7-12}$-arylalkyl; and m is 5-50, or preferably 10-40. The number average molecular weight as determined by GPC is suitably 500-3.000.

One or more cross-linking agents of formula (II) may be used in the cross-linking reaction.

In one embodiment of the invention, a mixture of one or more cross-linking agents of formula (II) comprising 3 or more Si—H groups and a polysiloxane chain extender comprising up to 2 Si—H groups is used in the cross-linking reaction.

The polysiloxane chain extender is suitably a compound having the formula $$R^3-SiO(R^3,R^3)-(SiO(R^3,R^3))_m-Si-(R^3,R^3,R^3) \quad (III)$$

wherein up to 2 of the groups $R^3$ are hydrogen and the rest of the groups $R^3$ are each independently selected from $C_{1-12}$-alkyl, $C_{3-8}$-cycloalkyl, $C_{6-14}$-aryl, and $C_{7-12}$-arylalkyl; and m is 0-50. The number average molecular weight as determined by GPC is suitably between 200 and 65.000, most preferably between 200 and 17.500.

As used herein $C_{1-12}$-alkyl means a linear or branched alkyl group having 1 to 12 carbon atoms, $C_{1-18}$-alkyl means a linear or branched alkyl group having 1 to 8 carbon atoms, and $C_{1-6}$-alkyl means a linear or branched alkyl group having 1 to 6 carbon atoms, such as methyl, ethyl, propyl, isopropyl, butyl, pentyl and hexyl.

As used herein $C_{1-4}$-alkylene means a linear or branched divalent alkylene group having 1 to 4 carbon atoms, such as methylene, ethylene, propylene, isopropylene, butylenes and isobutylene.

As used herein $C_{3-8}$-cycloalkyl means a cyclic alkyl group having 3-8 carbon atoms, such as cyclopentyl and cyclohexyl.

As used herein $C_{6-14}$-aryl means a phenyl or naphthyl group optionally substituted with $C_{1-6}$-alkyl, such as tolyl and xylyl.

As used herein $C_{7-12}$-arylalkyl means aryl attached to a $C_{1-6}$-alkyl group, where $C_{1-6}$-alkyl and aryl is as defined above, such as benzyl, phenethyl and o-methylphenethyl.

In the compound of formula (II) and in the compound of formula (III), the groups R and $R^3$, which are not hydrogen, are suitably each independently selected from a member of the group $C_{1-6}$-alkyl, $C_{6-14}$-aryl or $C_{7-12}$-arylalkyl.

The Si—H groups may be situated at either end of the compound of formula (II). However, at least one Si—H group is preferably positioned within the $-(SiO(R^3,R^3))_m-$ chain of the compound of formula (II).

The polysiloxane cross-linking agent and the chain extender may be prepared as described in Japanese Patent Application No. 2002-224706 and WO No. 05/032401 or analogously to the methods described therein.

An addition reaction is, in its simplest terms, a chemical reaction in which the atoms of an element or compound react with a double bond or triple bond in an organic compound by opening up one of the bonds and becoming attached to it, forming one larger compound. Addition reactions are limited to chemical compounds that have multiple-bonded atoms. Hydrosilylation is an addition reaction between, for example, a carbon-carbon double bond in a compound and a reactive hydrogen from a hydrogen siloxane.

Suitable addition reaction catalysts are any hydrosilylation catalysts, preferably platinum (Pt) catalysts. Pt-catalysts for the first part of the two-component sealant are described in U.S. Pat. No. 6,248,915. In consideration of toxicity potential, Pt complex catalyst where Pt is at a valency state of zero is preferred. Preferred catalysts are platinum-vinylsiloxanes and platinum-olefin complexes, such as Pt-divinyl tetramethyl disiloxane.

The reaction is suitably carried out neat at a temperature between 25° C. and 150° C. It is not necessary to use a solvent for the reaction, which is an advantage for any adhesive, but especially for skin applications.

Suitably, the ratio of the number of reactive Si—H groups in the polysiloxane cross-linking agent to the number of unsaturated groups in the polypropylene oxide, which are reactive with Si—H groups under the reaction conditions, is between 0.2 and 1.0.

The amount of polysiloxane used for the cross-linking is suitably less than 15% w/w and more preferred below 10% w/w of the amount of polyalkylene oxide polymer having unsaturated end groups.

The cross-linking reaction does not lead to complete cross-linking of all the polyalkylene oxide polymers. The adhesive comprises a mixture of cross-linked and non cross-linked polyalkylene oxide polymer.

The adhesive composition of the ostomy appliance according to the invention may contain other conventional ingredients for adhesive compositions, such as tackifiers, extenders, non-reactive polymers, oils (e.g. polypropylenoxide, ethyleneoxide-propyleneoxide copolymers, mineral oil), plastizisers, fillers, and surfactants. The adhesive may also comprise pharmaceutically active ingredients. These optional ingredients may be present in the reaction mixture during the cross linking reaction.

It may be advantageous that the soft adhesive comprises absorbent particles. The particles may be absorbent articles such as mineral salt, hydrocolloid, microcolloids or super absorbers in order for the adhesive to absorb moisture from skin.

Microcolloid particles are well known in the art e.g. from International Patent Application No. WO 02/066087, which discloses adhesive compositions comprising microcolloid particles. The microcolloid particles may have a particle size of less than 20 microns.

The collecting pouch may be detachable from the adhesive wafer by a coupling system or the pouch and the wafer may be integrated with the wafer, e.g. by welding. The two versions are known as one piece or two-piece appliances for ostomy.

The wafer of the device of the invention may have different shapes, such as circular, oval, square or user defined shape and the same applies for the attachment zone as well as the aperture.

In order to avoid rolling up of the edge portion during wear, it may be advantageous to bevel the edge portion of the wafer.

DESCRIPTION OF THE PREFERRED EMBODIMENTS

The invention is now explained more in detail with reference to the drawings showing preferred embodiments of the invention.

Figures 3A, 3B:
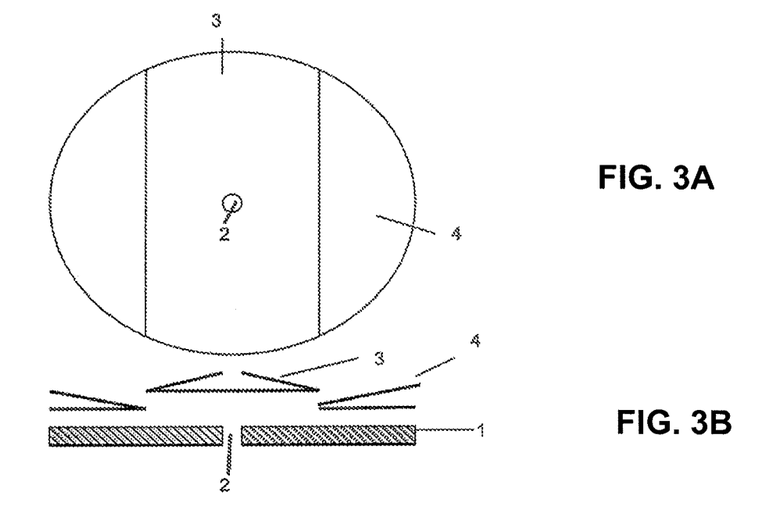
FIG. 3A is a wafer according to a third embodiment of the present invention seen from the skin-facing side thereof.
FIG. 3B is an exploded cross-sectional view of the wafer shown in FIG. 3A.
Figures 4A, 4B:
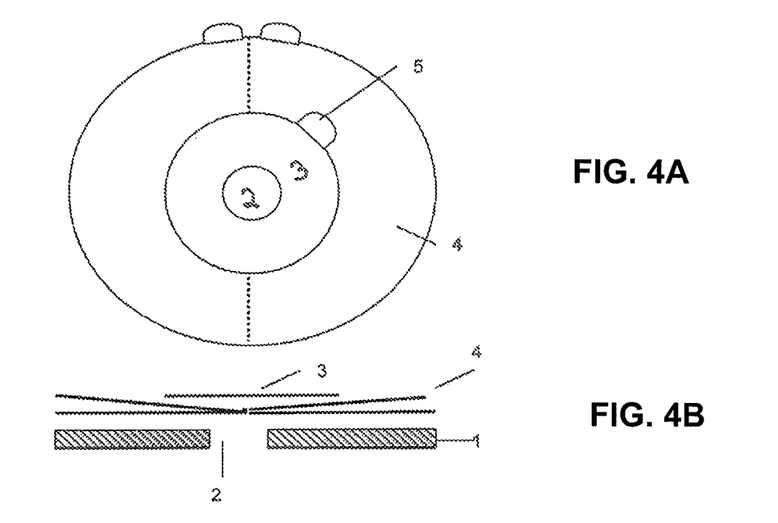
FIG. 4A is a wafer according to a fourth embodiment of the present invention seen from the skin-facing side thereof.
FIG. 4B is an exploded cross-sectional view of the wafer shown in FIG. 4A.
Figure 5A:
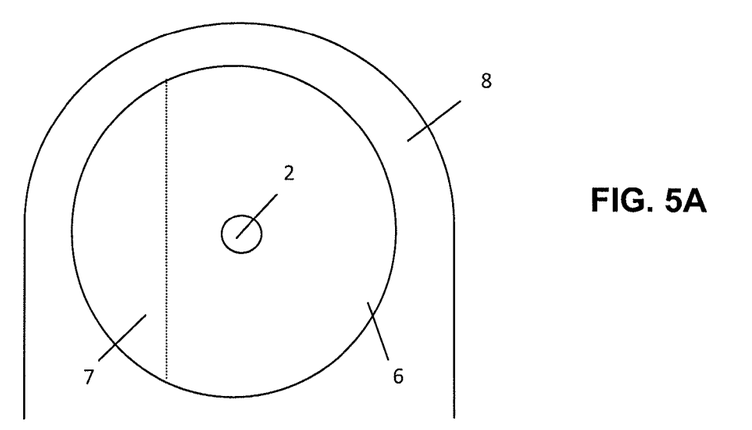
FIG. 5A is a wafer according to a fifth embodiment of the present invention seen from the skin-facing side thereof.
Figure 5B:
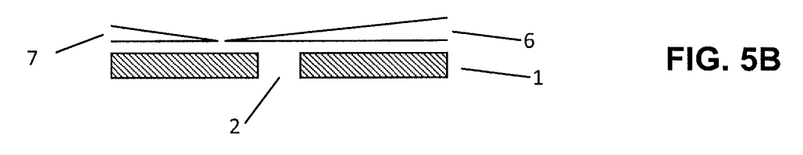
FIG. 5B is an exploded cross-sectional view of the wafer shown in FIG. 5A.

FIGS. 1A-5B show wafers of embodiments of ostomy appliances according to the invention. Each Figure designated with an "A" shows an embodiment of the wafer according to the present invention seen from the skin-facing side. Each Figure designated with a "B" shows the wafer of the corresponding "A" view in an exploded cross-section. By "corresponding" is meant Figures having the same number. For clarity, the wafers in FIGS. 1A through 4B are shown without attached coupling means or collection pouch mounted in the non-skin-facing surface of the wafer. FIGS. 5A and 5B include the collecting pouch.

Figures 1A, 1B:
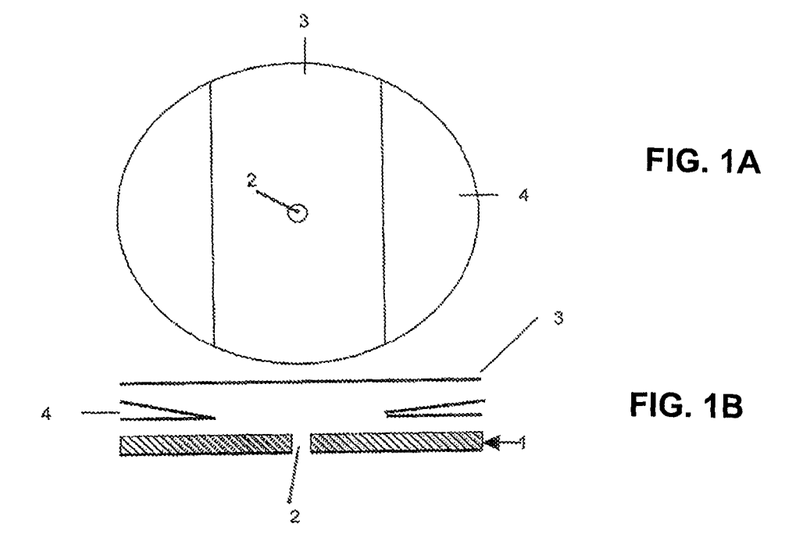
FIG. 1A is a wafer according to a first embodiment of the present invention seen from the skin-facing side thereof.
FIG. 1B is an exploded cross-sectional view of the wafer shown in FIG. 1A.

FIGS. 1A and 1B show a wafer (1) with a central aperture (2) for receiving a stoma, the wafer being provided with a three-split release liner system, comprising two side liners (4) covering the side portions of the adhesive surface and the third middle release liner (3) covering the middle portion of the adhesive wafer. By middle portion is meant the area from diametrical edge to edge and including the central portion of the wafer. The side release liners (4) are optionally folded in order to ease grip and detachment. The release liners can optionally be provided with an ear for easy removal. The middle liner may preferably overlap some or all of the side liners and may have folded edge portions, as shown in FIGS. 3A and 3B, to facilitate easy grip.

Figure 2A:
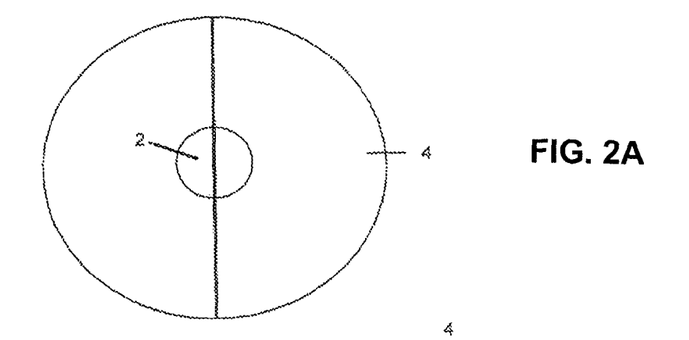
FIG. 2A is a wafer according to a second embodiment of the present invention seen from the skin-facing side thereof.
Figure 2B:
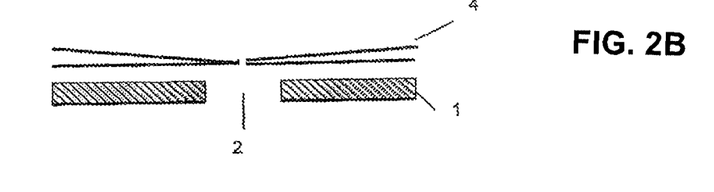
FIG. 2B is an exploded cross-sectional view of the wafer shown in FIG. 2A.

FIGS. 2A and 2B show a two-split release liner system where two side release liners (4) each cover half of the adhesive surface of the wafer (1). The liners are preferably folded to provide easy grip. For application the user may pull one or both lines away from the aperture, gradually exposing the adhesive surface and attaching said surface to the skin. The wafer is easily handled and applied as the adhesive is exposed gradually and the remaining part still has stiffness from the remaining part of the release liners. When the unprotected part of the skin-facing adhesive is placed on the skin, the rest of the release liners are rolled off and removed.

FIGS. 4A and 4B disclose an embodiment of the invention where the wafer (1) is provided with side liners (4) and a central liner (3) covering the central part of the wafer. By the central part is meant the area surrounding the aperture (2). The separately removable central release liner (3) may be in form of a ring, oval or angular (e.g. triangle, square or pentangle) shape intended for removal first. The wafer is then fastened to the skin around the stoma and subsequently the side liners may be rolled off.

FIGS. 5A and 5B disclose an embodiment of the invention comprising a wafer (1), an aperture (2), two release liners (6,7), and a collection pouch (8). The two release liners are organized asymmetrically over the wafer. The collection pouch is mounted on the non-skin-facing surface of the wafer.

Methods

Determination of Mechanical Properties of Adhesive Wafer

For measuring softness of the wafer, the testing guidelines from standard ISO527-1 were used. However, the parameters defined in ISO527-1 are in it self not sufficient to describe the relevant parameters for ostomy devices exactly. An ostomy device is placed on the stomach, on skin that can easily deform more than 20%. The relevant deformation for a soft adhesive wafer is in the same magnitude and we have therefore defined softness (modulus) of adhesive wafer as the force in Newton at 20% deformation divided by initial sample width. We used 'dog-bone' test specimens similar to the ones described in ISO 527-2 FIG. 1, but with different dimensions to accommodate the fact that some adhesive wafers are too small to be tested with ISO 527-1. We used test samples that corresponded with the samples from ISO527.2 FIG. 1, but where the width $b_1$ of the narrow portion was 4 mm and Gauge length $L_0$ was 10 mm. Relative deformation $\epsilon$ was calculated as the absolute deformation $\Delta L$ divided by the initial length $L_0$ as described in ISO 527-1. The rate of deformation was set to 1 mm/s. To accommodate the fact that some layers are isotropic, samples were measured in the softest direction. The obtained values are averages of at least 3 measurements.

Determination of G*.

The parameter G* or complex modulus as defined in "Dynamics of polymeric liquids", Vol. 1, sec. ed. 1987, Bird, Armstrong and Hassager, John Wiley and Sons inc., was used as a measure of the hardness/softness of an adhesive. G* at 32° C. and 0.01 Hz was measured as follows: A plate of un-foamed adhesive material was pressed into a plate of 1 mm thickness. A round sample of 25 mm in diameter was cut out and placed in a RheoStress RS600 rheometer from Thermo Electron. The geometry applied was parallel plates 25 mm and the deformation was fixed at 1% to ensure that measurements were in the linear regime. The measurement was carried out at 32° C.

The invention claimed is:

1. An ostomy appliance for attachment to a stoma body comprising a soft adhesive wafer and a collecting pouch attachable to the adhesive wafer at an attachment zone thereof, wherein the wafer includes a backing layer and a skin-facing adhesive layer with an adhesive surface, the adhesive surface of the wafer having a three split release liner system, with two folded side liners not covering the middle section of the wafer and with a third middle liner having folded edge portions and covering the middle portion of the adhesive surface having the same width as the attachment zone for the pouch or narrower, the release liners each covering at least a part of the adhesive surface and together these liners covering the entire adhesive surface, said wafer having a tensile strength at 20% strain of less than 0.75N/4 mm.

2. The ostomy appliance according to claim 1, wherein the release liners are organised symmetrically over the wafer.

3. The ostomy appliance according to claim 1, wherein the release liners are organised asymmetrically over the wafer.

4. The ostomy appliance according to claim 1, wherein the release liners are siliconised.

5. The ostomy appliance according to claim 1, wherein the adhesive has a $G^*$ at 0.01 hz of less than 15000 Pa.

6. The ostomy appliance according to claim 1, wherein the adhesive has a $G^*$ at 0.01 hz of less than 7500 Pa.

7. The ostomy appliance according to claim 1, wherein the adhesive comprises ethylene vinyl acetate.

8. The ostomy appliance according to claim 1, wherein the backing layer is in the form of a polymer film, coating, laminate, textile or non-woven.

9. The ostomy appliance according to claim 1, wherein the backing layer has a force below 0.75 N/4 mm at 20% extension.

10. The ostomy appliance according to claim 1, wherein the collecting pouch is detachable.

11. The ostomy appliance according to claim 1, wherein the collecting pouch is integrated with the wafer.

12. The ostomy appliance according to claim 1, wherein the backing layer has a force below 0.5 N/4 mm at 20% extension.

13. The ostomy appliance according to claim 1, wherein the adhesive comprises a polyalkyleneoxide polymer and an organosiloxane based cross-linked adhesive system.

14. The ostomy appliance according to claim 13, wherein the polyalkylene oxide polymer is polypropyleneoxide.

* * * * *